United States Patent [19]
Rosen

[11] Patent Number: 5,094,231
[45] Date of Patent: Mar. 10, 1992

[54] ORTHOPEDIC SHOE RESTRAINT

[76] Inventor: Alan Rosen, 1409 Park St., Atlantic Beach, N.Y. 11509

[21] Appl. No.: 633,672

[22] Filed: Dec. 26, 1990

[51] Int. Cl.$^5$ .............................................. A61F 5/00
[52] U.S. Cl. ....................................... 602/24; 128/882
[58] Field of Search ................ 128/80 R, 80 A, 80 B, 128/84 A, 87 C, 882; 70/18; 272/142

[56] References Cited

U.S. PATENT DOCUMENTS

| | | | |
|---|---|---|---|
| 2,835,249 | 5/1958 | Brandano | 128/882 |
| 2,963,020 | 12/1960 | Moran | 128/80 A |
| 3,109,424 | 11/1963 | Brachman | 128/80 A |
| 3,265,063 | 8/1966 | Friedman | 128/80 A |
| 3,477,426 | 11/1969 | Wincheski | 272/142 X |
| 3,487,829 | 1/1970 | Barnett | 128/80 R |
| 3,523,526 | 8/1970 | Phelps | 128/80 R |
| 3,892,231 | 7/1975 | Tummillo | 128/80 A |
| 3,931,817 | 1/1976 | Infranca | 128/80 A |
| 4,040,416 | 8/1977 | Zentman | 128/80 A |
| 4,263,901 | 4/1981 | Nichols | 128/80 A |
| 4,520,803 | 6/1985 | Quest | 128/80 A |
| 4,570,620 | 2/1986 | Kurtz et al. | 128/80 A |
| 4,606,334 | 8/1986 | Salmon | 128/80 A |

FOREIGN PATENT DOCUMENTS

| | | | |
|---|---|---|---|
| 8303194 | 9/1983 | PCT Int'l Appl. | 128/80 A |
| 2133289 | 7/1984 | United Kingdom | 128/87 C |

Primary Examiner—Richard J. Apley
Assistant Examiner—Linda C. M. Dvorak
Attorney, Agent, or Firm—Robert W. Fiddler

[57] ABSTRACT

An orthopedic device for securement to the shoes of a patient to be treated to limit the relative angulation between the shoes, and to limit the relative spacing between the shoes while permitting some up and down movement of the feet. The device is formed with an elongate connecting member, with securing elements, one at each end thereof, with at least one of the securing elements being selectively detachable. Anchoring elements are provided on said shoes for pivotal engagement by said securing elements, with the anchoring elements adapted for affixation to the shoes of a patient. The anchoring elements and securing elements are pivotally interengaged, with a combined length less than the length of the shortest of the connected shoes, whereby the connected shoes may be moved up and down and at an angle to each other, while limiting the relative spacing between the shoes, and the possible range of movement of the shoes from a position substantially parallel to each other to one in which the feet of the patient have been rotated from a substantially parallel position.

17 Claims, 2 Drawing Sheets

U.S. Patent     Mar. 10, 1992     Sheet 1 of 2     5,094,231
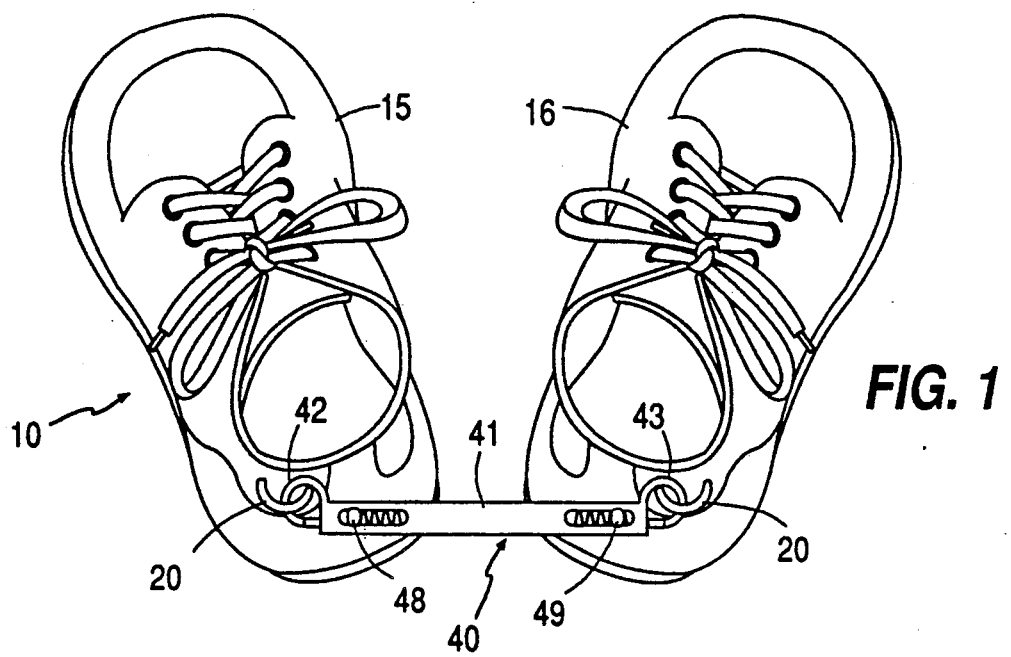
*FIG. 1*
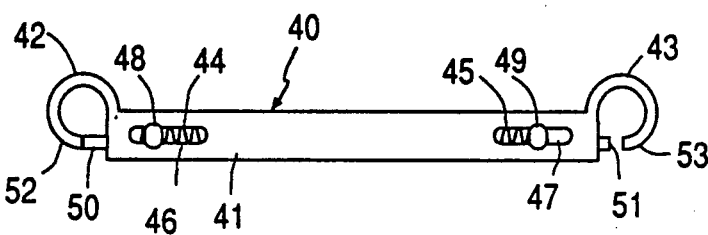
*FIG. 2*
*FIG. 3*
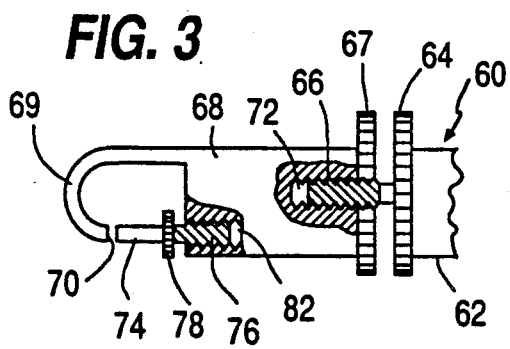
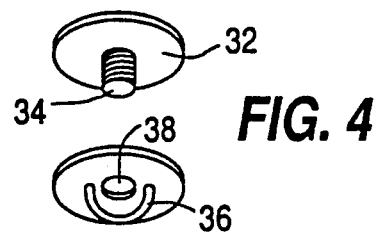
*FIG. 4*
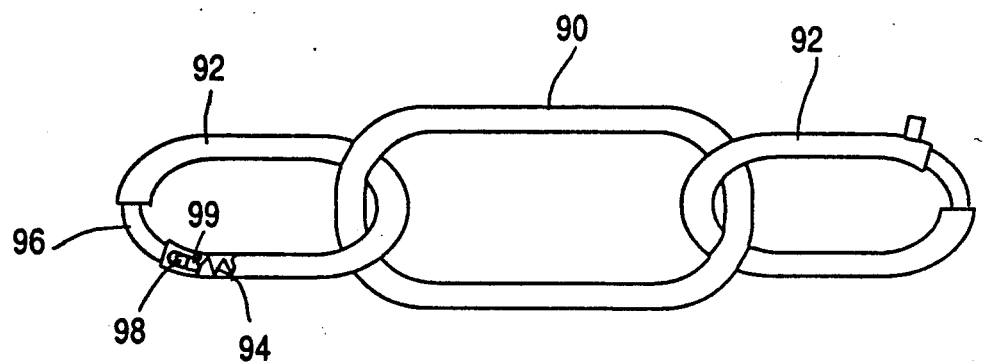
*FIG. 5*

5,094,231

ORTHOPEDIC SHOE RESTRAINT

This invention relates to corrective orthopedic devices for the treatment of limb deformities, and more particularly to a device for correcting rotational leg and foot deformities.

BACKGROUND OF THE INVENTION

There are a variety of limb deformities of both a congenital and/or acquired nature due to skeletal, muscle, tendon or nervous system defects.

In the treatment of these defects, a variety of braces have been evolved over the years for purposes of limiting the range of motion of the wearer's feet relative to each other.

Fixed bracing of the legs of the wearer to immobilize the legs has come to be recognized as undesirable for most treatment. The present trend in orthopedic treatment is to provide some sort of appliance which will limit the relative movement of the feet of the wearer, while at the same time permitting some movement for purposes of exercise and the maintenance of muscle tone in the restricted limbs, as shown for example by U.S. Pat. Nos. 1,136,150; 2,963,020; 3,477,426; and 3,487,829.

However, these above referenced prior art braces, though permitting some relative movement of the feet of the patient, employ relatively complex structures requiring relative skill in the adjustment and in securement of the braces to the shoes or feet of the patient.

SUMMARY OF THE INVENTION

It is with the above considerations in mind that the present improved orthopedic device has been evolved, employing a pair of conventional shoes of a type which may be worn by a patient requiring treatment. A coupling is provided between the shoes such as to limit the possible range of rotation (about a longitudinal leg axis) of the feet of the patient wearing the shoes, while at the same time permitting relative up and down movement of the feet of the wearer, and subject to relatively simple attachment to the shoes of the wearer, and selective removal to facilitate dressing of the patient.

It is accordingly among the primary objects of this invention to provide a simple orthopedic device subject to relatively inexpensive fabrication, and subject to ready use at minimum expense, and requiring minimum skills for use.

Another object of the invention is to provide an orthopedic device particularly adapted to be used in the correction of an inward or outward deformity of the ankle or tibia of a patient.

An additional object of the invention is to provide an orthopedic device particularly adapted to provide tibial torsion, metatarsis adduction and post surgical retainment.

It is also an object of the invention to provide an orthopedic device which is relatively comfortable for an infant patient.

Another object of the invention is to provide an orthopedic device lending itself to easy attachment and detachment to facilitate dressing and changing of diapers of an infant patient.

It is also an object of the invention to provide an orthopedic device particularly for infants which will not damage bedding in a crib or carriage with which the device comes into contact.

A further object of the invention is to provide an orthopedic attachment which is aesthetically unobtrusive.

These and other objects of the invention which will become hereafter apparent are achieved by providing a detachable connecting member having a securing element at each end thereof, each securing element adapted for pivotal engagement with an anchoring element positioned on a conventional shoe. At least one of these securing elements on the connecting member is preferably made selectively releasable so as to facilitate disengagement of the shoes for dressing of the patient, or the like. The connecting member may be made either of a fixed length or of a selectively adjustable length by forming it of an interengageably threaded socket and stud or the like, with the length of the connecting member and its associated engaging elements being less than that of the shoes to which attached. As a result, the feet of a patient to whom the connected shoes have been applied are limited in movement from a position in which the feet are substantially parallel, to a position in which the feet are rotated about the pivot connection with the foot ends remote from the anchoring element moved outwardly to a substantially non-parallel position.

A feature of the invention resides in the fact that a variety of off-the-shelf hardware elements may be employed in practicing the invention, so as to minimize expense.

Another feature of the invention resides in the fact that relatively familiar elements may be employed, avoiding the strangeness and possible offensiveness of typical orthopedic appliances.

BRIEF DESCRIPTION OF THE DRAWINGS

The specific details of some preferred embodiments of the invention will be described in clear, concise and exact terms so as to enable any person skilled in the art to practice the invention, setting forth the best mode contemplated by applicant in conjunction with the accompanying drawings, wherein:

FIG. 1 is a perspective view of the improved orthopedic device showing one form of connecting member and anchoring element applied to a pair of baby shoes;

FIG. 2 is an elevational view of a connecting member as employed in FIG. 1, with parts broken away to show the spring pressed plungers;

FIG. 3 illustrates a partial view of another embodiment of the connecting member, with parts broken away to show some suggested threading arrangements;

FIG. 4 illustrates a form of anchoring element;

FIG. 5 illustrates another form of connecting member;

DESCRIPTION OF PREFERRED EMBODIMENTS OF THE INVENTION

Referring now more particularly to the drawings, where like numerals in the various figures will be employed to designate like parts, the orthopedic device 10 embodying the invention is illustratively shown as comprising a conventional pair of children's shoes, here shown as left shoe 15 and right shoe 16 of the same size, as conventional, though it is recognized that different shoe sizes may be employed.

Figure 8:
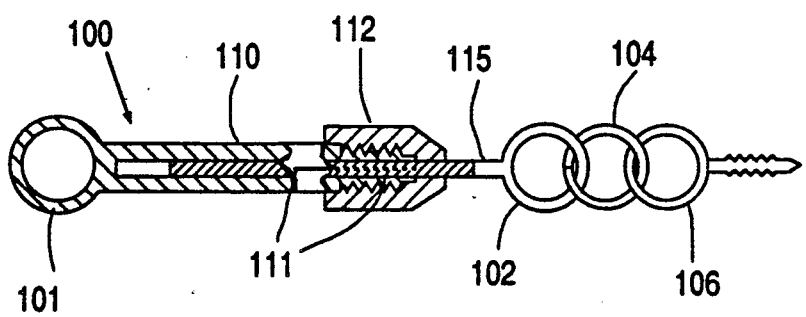
FIG. 8 illustrates a proposed variable extension arrangement to facilitate selective variation of the length of the connecting member.

Anchoring elements 20 are illustratively shown as secured to an outer rear quadrant of the shoe. These anchoring elements may take the form of flexible loops formed of cord, wire, leather, plastic or the like, as shown in FIG. 1, or as rigid eyelets or hasps 30 as shown in FIG. 4, or as screw eyes or spring rings as shown in FIG. 8. As will be apparent to those skilled in the art, anchoring elements may take a variety of forms and are intended to be such as to permit ready securement of the anchoring element to the shoe and subject to having a pivotal connection formed therewith. These anchoring elements 20 have been illustratively shown as flexible loops sewn or otherwise secured to the side wall of the shoe as in FIG. 1, or as a washer supported hasp 30 as shown in FIG. 4. Alternatively, a conventional screw eye as shown in FIG. 8 may be anchored into the sole of the shoe, or a screw eye and nut may be employed for affixation to the side wall of the shoe, or a spring ring as shown in FIG. 8 may be threaded through the shoe sidewall.

In the FIG. 4 embodiment of the anchoring element, a base washer element 32 is shown intended for positioning on the interior of a shoe, and a threaded stud 34 is extended from the base washer 32 through a hole formed in the wall of the shoe dimensioned to accommodate the threaded stud 34. An outer washer plate 36 to which hasp 30 is secured is provided with a central threaded opening 38 designed to engage the threads on stud 34. In use, as will be understood by those skilled in the art, the inner base washer is positioned inside the shoe with the threaded stud 34 extending through an appropriate opening in the wall of the shoe, and the outer washer plate 36 is screwed into threaded engagement with the stud 34 to sandwich the shoe material between the inner base washer 32 and the outer washer plate 36 to retain the hasp 30 in fixed position with respect to the shoe.

A connecting member of one of the forms illustratively shown in FIGS. 1, 2, 3, 5 and 8 is provided for selective coupling to the anchoring elements.

The connecting member 40 illustratively shown in FIG. 1 and 2 is provided for engagement with the anchoring elements applied to the shoes 15 and 16. The connecting member 40 is of an elongate configuration, and is of a length less than the length of any one of the shoes 15 and 16 between which the connecting member is positioned. The connecting member 40 is illustratively shown as formed with an elongate cylindrical rod shaped body 41 having a securing element 42 and 43 respectively at each opposed end thereof. In the embodiment of the connecting member 40, as illustrated in FIGS. 1 and 2, the elongate body 41 of the member is shown as formed with a hollow interior for accommodating springs 44 and 45, and formed with slideways 46 and 47 and actuating buttons 48 and 49 respectively. Plungers 50 and 51 are secured to the buttons 48 and 49, which are adapted to move to and from the inturned ends of the securing elements 42 and 43. As will be apparent to those skilled in the art, the plungers 50 and 51 may be moved against the action of the springs 44 and 45 respectively to bring them to or from the anvil faces of inturned ends 52 and 53, the plunger 50 on the left of FIG. 2 being shown in engagement with the anvil face of inturned end 52, and the plunger 51 shown spaced from the anvil end of inturned end 53.

Alternatively, as shown in FIG. 3, a connecting member 60, one end of which is shown, may be formed from an elongate body 62, only one end of which is shown. This rod-shaped body 62 is formed with a knurled knob 64 and a threaded stud 66 extending therefrom. Lock nut 67 is preferably threaded on stud 66. A securing element 68 is formed with a hooked end 69 having an anvil face 70. Securing element 68 is formed with a threaded opening 72 dimensioned to interengage with threaded stud 66 on body 62. A plunger 74 is provided for mating against anvil 70. Plunger 74 is formed with a threaded end 76 and a knurled knob 78. The threaded end 76 of plunger 74 is arranged in threaded opening 82 in securing element 68, as a result of which rotation of knurled knob 78 brings plunger 74 to or from anvil 70. The length of the connecting member may be selectively varied by rotating body 62 to thread stud 66 into or out of engagement with the threads in opening 72, with knurled lock nut 67 brought to bear against the end of body 62 to fix the selected relative position of body 62 and securing element 68.

Another form of connecting members shown is in FIG. 5, in which a continuous elongate chain link 90 is coupled to identical securing elements 92. The securing elements 92 as illustratively shown are formed as split rings with a hollow end having a spring 94, as shown in the broken portion at the end of the left hand portion of 92. The spring 94 engages plunger 96, which is formed with a lateral extending actuating pin 98 positioned to ride in slot 99 in a fashion like the spring pressed plunger structure illustrated in FIG. 2.

In the embodiment of the connecting member 100 shown in FIG. 8, the member 100 is formed with securing elements in the form of ring ends 101 and 102 adapted for engagement by split spring opening rings 104 secured to the sidewall or soles of the shoes. Spring rings 104 may be threaded through openings in the shoe sidewall, or secured to a screw eye 106, the screw ends of which are threaded into the shoe sidewall or sole. Connecting member 100 is formed with a hollow body portion 110, with ring end 101 illustratively shown as formed integrally therewith. The end of body portion 110 remote from ring end 101 is split at 111, threaded and tapered. An externally knurled chuck cap 112 is internally threaded and tapered to fit over the threaded tapered end of body 110 so that threading of the chuck cap 112 over the body end will open or close slit 111. Within the hollow body portion, extension rod 115 is slidably mounted. Extension rod 115 is formed with ring end 102 which is illustratively shown in engagement with spring ring 104, engaging screw eye 106.

OPERATION

In use, the desired form of the above described structures is fabricated employing conventional techniques employed for fabricating these structures. Thus, the shoes 15 and 16 are conventional infant shoes. It will be apparent to those skilled in the art that the type of shoe employed is not limited to that illustrated, and though the orthopedic condition in connection with which the instant invention is employed will usually be applied to infants so as to correct deformity as early as possible, it may obviously be employed on older patients.

The connecting members and anchoring elements as illustratively shown and described, though here described as of a preferred type, may readily be of a type such as conventionally available in a hardware store.

Appropriate anchoring elements, either in the form shown in FIGS. 1 or 4 or in the form of a screw eye as shown in FIG. 8, washer and hasp, screw ended hasp or spring ring as shown in FIG. 8 are secured to the side walls or sole of the shoe of the patient. A connecting member of a type such as shown in FIGS. 2, 3, 5 or 8 is extended between the anchoring element which has been secured to the shoe. The length of the connecting member should be such as to prevent the end of the shoe opposite to that to which the connecting member is attached from turning in upon itself. This is most readily accomplished be making the connecting member of a length less the length of the shortest shoe of the pair to which attached.

Figure 6:
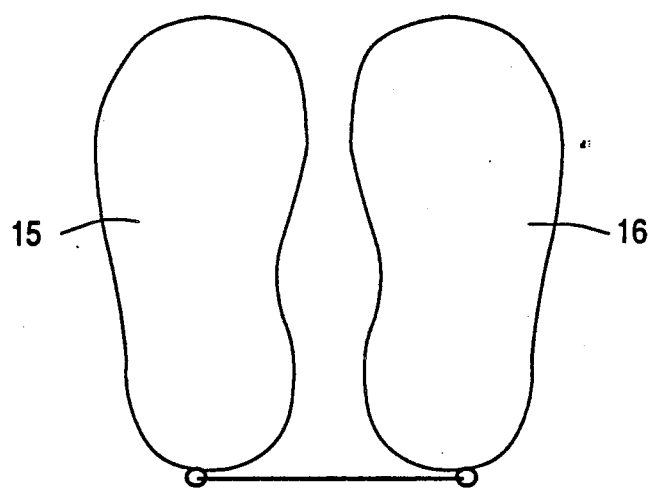
FIG. 6 shows a schematic view of one of the preferred limiting positions of the feet of a patient wearing the orthopedic device in which the feet of the patient are substantially parallel to each other.
Figure 7:
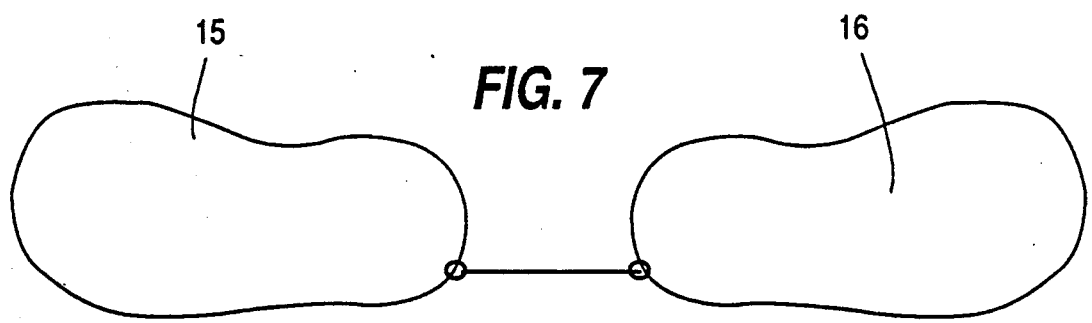
FIG. 7 shows a schematic view of the other of the possible positions to which the feet of a patient wearing the orthopedic device in which the feet of the patient have been rotated out to an angle of 180° to each other.

As a result of this limited length, though the feet of the wearer may be pivoted with respect to each other, both in the plane of the soles of the shoe, and up and down out of the plane of the soles of the shoe to permit exercise and movement of the feet of the wearer, the range of rotational movement of either given foot about the axis of its leg is limited from a position in which the shoes are forwardly pointed and substantially parallel to each other, as shown in FIG. 6, to a position in which the feet of the wearer are rotated outwardly from the forwardly facing substantially facing parallel position, to a position at 180° to each other as shown in FIG. 7.

The above disclosure has been given by way of illustration and elucidation, and not by way of limitation, and it is desired to protect all embodiments of the herein disclosed inventive concept with the scope of the appended claims.

What is claimed is:

1. An orthopedic device for correcting limb deformities, said device comprising:
   a pair of shoes dimensioned to fit the feet of the patient to be treated;
   a pair of anchoring elements affixed, one on the exterior of an end area above the bottom of each shoe of said pair of shoes;
   an elongate connecting member of a length less than the length of the shortest of the shoes of said pair, extended between the ends of said shoes to which said anchoring elements are affixed; and
   securing elements, one at each end of said elongate connecting member pivotally engaging an anchoring element on said shoes, wherein, when the securing elements are engaged with said anchoring elements, the possible range of movement of the shoes will be from a position in which the feet of the patient to whom the device has been applied are forwardly facing and substantially parallel to each other, to a position in which the ends of the feet of the patient opposite to the end of the shoe to which said connecting member is secured are rotated about the longitudinal leg axis of the patient from a substantially parallel position.

2. An orthopedic device as in claim 1 in which said anchoring element is affixed at some point on the surface of the rear half of the shoe.

3. An orthopedic device as in claim 1 in which said anchoring element is in the form of a loop member secured to said shoe.

4. An orthopedic device as in claim 1 in which an anchoring element is secured to an outer rear quadrant of each shoe.

5. An orthopedic device as in claim 1 in which said anchoring element comprises a loop formed of a length of cord or wire extending from spaced points on the exterior surface of each shoe.

6. An orthopedic device as in claim 1 in which said anchoring element comprises:
   a base washer element;
   a threaded stud extended from said washer;
   an outer washer having a threaded opening dimensioned to accommodate said stud; and
   a hasp secured to said outer washer on the face therof remote from said inner washer.

7. An orthopedic device as in claim 1 in which said connecting member comprises:
   an elongate rod-shaped body; and
   a securing element at each opposed end therof.

8. An orthopedic device as in claim 7 in which at least one of said securing elements comprises a hook-shaped extension from said body of said connecting member.

9. An orthopedic device as in claim 8 in which the end of said hook-shaped extension forms an anvil; and said elongate body is formed with a hollow containing a spring pressed plunger with an outer end bearing against said anvil.

10. An orthopedic device as in claim 7 in which said connecting member is formed with a threaded stud extending from an end thereof; and at least one of said securing elements is formed with an internally threaded opening dimensioned to accommodate said threaded stud.

11. An orthopedic device as in claim 10 in which at least one securing element is formed of a hook-shaped configuration, with the end of the hook forming an anvil face; and a plunger having a threaded end inserted into a threaded opening in said securing element, with the end of said plunger opposite said threaded end arranged to selectively bear against said anvil face.

12. An orthopedic device as in claim 1 in which said connecting member comprises an elongate chain link.

13. An orthopedic device as in claim 12 in which said securing elements comprise split rings engaged with said elongate link, said split rings adapted for selective securement, one to each anchoring element on each shoe.

14. An orthopedic device as in claim 13 in which said split rings are provided with a hollow at one end of the ring adjacent the split, with a spring pressed plunger positioned in said hollow for movement against the opposite end of the split ring.

15. An orthopedic device as in claim 1 in which said anchoring element comprises a screw-eye, the screw end of which is threaded into said shoe.

16. An orthopedic device as in claim 1 in which said anchoring elements comprise a split spring ring.

17. An orthopedic device as in claim 1 in which said connecting member comprises:
   a hollow body portion having a split externally threaded tapered end;
   an internally threaded and tapered chuck cap engaging over the threaded end of said body portion; and
   an extension rod slideably positioned in the hollow of said body portion.

* * * * *